United States Patent [19]

Yoshida

[11] 4,341,866

[45] Jul. 27, 1982

[54] ANTIENZYME TERMINATION IN ENZYME IMMUNOASSAYS

[75] Inventor: Robert A. Yoshida, San Diego, Calif.

[73] Assignee: Syva Company, Palo Alto, Calif.

[21] Appl. No.: 155,367

[22] Filed: Jun. 2, 1980

[51] Int. Cl.³ .................... G01W 33/54; C12W 9/99
[52] U.S. Cl. ........................ 435/7; 435/184; 435/810; 23/230 B; 424/12
[58] Field of Search ............. 435/7, 188, 184, 810; 424/8, 12; 23/230 B

[56] References Cited

U.S. PATENT DOCUMENTS

| | | | |
|---|---|---|---|
| 3,875,011 | 4/1975 | Rubenstein et al. | 435/26 |
| 4,233,401 | 11/1980 | Yoshida et al. | 435/7 |
| 4,234,680 | 11/1980 | Hevey et al. | 435/184 |

Primary Examiner—Thomas G. Wiseman
Attorney, Agent, or Firm—Bertram I. Rowland

[57] ABSTRACT

An improved method is provided for performing an enzyme immunoassay, where the signal producing compound is chemically labile. Particularly, in homogeneous enzyme immunoassays, where the enzyme is conjugated with a hapten, and an antibody binding to hapten reduces or inhibits the activity of the enzyme-hapten conjugate, the immunoassay is performed in accordance with conventional procedures. After a sufficient time, antienzyme is added which rapidly deactivates the enzyme, so that the signal remains constant for long periods of time.

9 Claims, No Drawings

ANTIENZYME TERMINATION IN ENZYME IMMUNOASSAYS

BACKGROUND OF THE INVENTION

1. Field of the Invention

In homogeneous enzyme immunoassays, as described in U.S. Pat. No. 3,817,837, one normally measures the change in level of the detectible signal over a predetermined relatively short time period. In many situations, it is desirable to be able to quench the reaction at the end of the predetermined interval and measure the result subsequently at one's leisure. However, the manner in which the enzyme reaction is quenched is subject to many constraints. First, the reaction must be stopped completely. One cannot allow for a slow continuous reaction, since the measurement would then become time dependent. Secondly, the manner in which the reaction is terminated must not affect the stability of the compound providing the detectible signal nor result in any transformation of the precursor which provides the product. Thus, where chemically labile compounds are involved in the production of the detectible signal, the nature of the quenching reaction is severely limited.

2. Description of the Prior Art

U.S. Pat. No. 3,817,837 describes a homogeneous enzyme immunoassay. Inhibition of enzymes by antibodies to enzymes is known. U.S. Pat. No. 3,654,090 is descriptive of heterogeneous enzyme immunoassays.

SUMMARY OF THE INVENTION

An improved method for performing enzyme immunoassays, particularly homogeneous, is provided, whereby after performing the immunoassay in accordance with conventional techniques, the reaction is quenched so that the final measurement need not be taken immediately at the end of a predetermined time interval. The use of antienzyme is found to substantially immediately inhibit any turnover of the enzyme without adversely affecting the stability of the observed signal level. Particularly, the enzyme glucose-6-phosphate dehydrogenase is employed with the detectible signal obtained by measurement of NADH or NADPH.

DESCRIPTION OF THE SPECIFIC EMBODIMENTS

In accordance with the subject invention, enzyme immunoassays, either homogeneous or heterogeneous, are performed in conventional manners, with the added convenience that a measurement need not be made at the end of the predetermined time interval. Rather, the reaction is quenched at the end of the predetermined time interval by the addition of antibodies which provides for a stable signal level for extended periods of time where labile signal producing compounds are involved, e.g. coenzymes.

In view of the ample literature describing enzyme immunoassays, only a brief description of the assay techniques will be made. The homogeneous assay is performed by combining in various orders, an enzyme-hapten conjugate, which when a receptor, usually an antibody for the hapten, binds to the hapten, the enzyme activity is substantially inhibited, normally not completely inhibited. One combines the sample suspected of containing the analyte, the enzymehapten conjugate, receptor, normally antibody for the hapten, and enzyme substrates, including co-factors, where the product of the enzymatic reaction provides for a detectible signal and is chemically labile. Particularly, the enzyme is a dehydrogenase, and a coenzyme, e.g. NADH or NADPH, is the compound that provides the signal.

The assay is normally performed in an aqueous medium at a pH in the range of about 6 to 10, where the concentrations of the enzyme-hapten conjugate and the receptor, as well as the ratio of enzyme-hapten conjugate and receptor are empirically determined, based on the concentration range of interest of the analyte and the chemical and physical characteristics of the enzyme-hapten conjugate and the receptor. The amount of antienzyme employed will be empirically determined, since it will depend upon the binding constant of the antienzyme, the percent of the antisera which is effective in providing inhibition, and the like.

In carrying out the assay, varying orders of addition may be employed prior to the introduction of the antienzyme. Conveniently, the sample can be combined with antiligand, followed by the addition of the enzyme-bound ligand and enzyme substrates including co-factors. The amount of enzyme substrates and co-factors will be in sufficient amount so as not to be rate limiting. That is, over the period of the assay, there will be a substantial excess of the substrates over the amount transformed.

The assay will be carried out normally at temperatures in the range of about 10° to 25° C., more usually in the range of about 15° to 40° C., and at a pH in the range of about 5 to 10, usually about 6 to 9. Various buffers may be employed, such as tris, carbonate, borate and phosphate. The medium is normally aqueous, with minor amounts of other polar solvents optionally present, usually in amounts not greater than about 40%.

In order to reduce serum-to-serum variation with serum samples, particularly with hydrophobic haptenic analytes, it will usually be desirable to employ a pretreatment. Desirably, a protease is employed at an acidic pH, particularly added in the form of a proenzyme, e.g. pepsinogen. A serum sample is combined with the acidic (pH1-3) protease pretreatment solution. The serum sample is combined with a sufficient amount of enzyme for a sufficient time, usually 20 to 45 min, to provide for substantial proteolytic degradation of the serum proteins. The proteolytic degradation is terminated by adding a sufficient amount of an alkaline solution to raise the pH to equal or greater than about 6.

With heterogeneous enzyme immunoassays, the enzyme-hapten conjugate does not undergo any substantial change in enzyme activity when antihapten is bound to the hapten. The antihapten will usually be bound to a support, which may be a wall, various particles or the like. The sample, enzyme-hapten conjugate and antihapten are combined, the enzyme-hapten conjugate bound to antihapten separated from unbound, and the enzyme activity determined of the unbound enzyme or the bound enzyme. See U.S. Pat. Nos. 3,654,090; 3,791,932; 3,839,153; 3,850,752 and 3,879,262, for descriptions of various techniques, the relevant portions of which are incorporated herein by reference.

The hapten monoepitopic ligand analytes will generally be from about 100 to 2,000 molecular weight, more usually from 125 to 1,000 molecular weight. The analytes of interest include drugs, metabolites, pestacides, pollutants, and the like. Included among drugs of interest are the alkaloids. Among the alkaloids are morphine alkaloids, which includes morphine, codeine, heroin, dextromethorphan, their derivatives and metabolites;

cocaine alkaloids, which includes cocaine and benzoyl ecgonine, their derivatives and metabolites; ergot alkaloids, which includes the diethylamide of lysergic acid; steroid alkaloids; iminazoyl alkaloids, quinazoline alkaloids, isoquinoline alkaloids; quinoline alkaloids; which include quinine and quinidine; diterpene alkaloids; their derivatives and metabolites.

The next group of drugs includes steroids, which includes the estrogens, gestogens, androgens, andrenocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propanolol, griseofulvin, valproic acid, butyrophenones, antihistamines, anticholinergic drugs, such as atropine, their metabolites and derivatives.

The next group of compounds is amino acids and small peptides which include polyiodothyronines e.g. thyroxine, and triiodothyronine, oxytocin, ACTH, angiotensin, met- and leu-enkephalin, their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

Of particular interest are steroids, including androgens, estrogens, progestogens, adrenocortical hormones, cardiac glycosides and aglycones and derivatives thereof.

The next group of drugs is lactams having from 5 to 6 annular members, which include the barbiturates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines, catecholamines, which includes ephedrine, L-dopa, epinephrine, narceine, papaverine, their metabolites.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, $B_{12}$, C, D, E and K, folic acid, thiamine.

The next group of drugs is prostaglandins, which differ by the degree of sites of hydroxylation and unsaturation.

The next group of drugs is antibiotics, which include penicillin, chloromycetin, antinomycetin, tetracycline, terramycin, their metabolites and derivatives.

The following examples are offered by way of illustration and not by way of limitation.

EXPERIMENTAL

EXAMPLE 1.

Conjugation of 3 ketodigoxigenin carboxymethyloxime to glucose-6-phosphate dehydrogenase (G6PDH)

Into a flask was charged 14.3 mg ($3.1 \times 10^{-2}$ mmole) 3-ketodigoxigenin carboxymethyloxime, 0.335 ml of dry DMF, 0.087 ml of 0.357 M N-hydroxysuccinimide (NHS) in dry DMF ($3.1 \times 10^{-2}$ mmole) and 0.080 ml of 0.387 M dicyclohexylcarbodiimide in dry DMF ($3.1 \times 10^{-2}$ mmole) in that order with agitation at room temperature. After flushing with argon, the flask was sealed and the mixture stirred overnight at 2°-4° C., following the course of the reaction with TLC on silica gel, irrigating with acetic acid/methanol/chloroform::0.5:1.0:10, the major product having $R_f$=0.56. The reaction mixture was filtered through a glass wool plug and used without further purification.

Lyophilized G6PDH (79.5 mg, 15-17% enzyme by weight) was dissolved in 3 ml ice-cold 0.055 M tris-HCl (pH 8.1), exhaustively dialyzed against the same buffer at 2°-4° C. and the residue enzyme solution adjusted to 5.0 ml with the same buffer to give 2.6 mg/ml G6PDH. Into the reaction flask was charged 4.0 ml ($1 \times 10^{-4}$ mmole) of the above described G6PDH solution, the mixture cooled with an ice bath and 0.10 g (0.294 mmole) of G6P.2Na.3H$_2$O and 0.160 g (0.210 mmole) of β-NADH added with agitation, followed by the addition of 2.16 ml of carbitol ® added slowly over 10 min. with good stirring and continued cooling. To the solution was then added a series of aliquots of a $6.18 \times 10^{-2}$ M solution of the NHS ester of the digoxigenin derivative, with stirring for 20 min. after each addition, followed by a determination of percent deactivation and percent inhibition of the enzyme. The following are the results with the first number being microliters of activated ester added, the second number being the percent deactivation and the third number being the percent inhibition: 28, 8.8, 16.8; 100, 31.4, 67.8; 25, 36.7, 73.5.

After the final addition, the conjugation mixture was spun down at 12,000×g for 10 min. at 2°-4° C. and the supernatant chromatographed on a 2.6×62 cm Sephadex G-25M column and eluted with 0.055 M tris-HCl (pH 8.1) at 2°-4° C. The column flowrate was 36 drops (2.6 ml) per minute and 60 drop (4.4 ml) fractions collected. Fractions 28 to 32 were pooled to give 22 ml of the desired conjugate. The conjugate had 75.3% inhibition with excess antidigoxin.

EXAMPLE 2

Antisera to glucose-6-phosphate dehydrogenase

Lyophilized G6PDH (29-32 mg) (see above for description) was dissolved in a minimal quantity (1 ml) of 0.010 M phosphate buffer plus 0.90% NaCl (pH 7.1) and exhaustively dialyzed against the same buffer 2°-4° C. The residue was diluted with the same buffer to 5 ml to give a 1.0 mg/ml G6PDH solution. This solution was used for injection in accordance with conventional techniques and sheep were immunized on a monthly basis with production bleeding commencing at the fourth bleed.

In order to demonstrate the subject invention, the following assays were carried out.

The following are the formulations of the reagents.

1. Pretreatment Concentrate when diluted 2-fold with Pretreatment Diluent gives Pretreatment Reagent which consists of:
   8.6 mg/ml pepsinogen
   0.0025 M Tris-HCl
   0.025% NaN$_3$
   0.10 M HCl
   0.15% Triton X-100
   where Pretreatment Concentrate is
   17.2 mg/ml pepsinogen
   0.005 M Tris-HCl
   0.05% NaN$_3$
   (pH 5.1); and is
   0.20 M HCl
   0.30% Triton X-100
   (pH ~1.49)

2. Antibody Reagent is a dilution of antianalyte IgG fraction in:
   0.055 M Tris-HCl
   0.05% NaN$_3$
   0.005% Na$^\oplus$ thimerosal
   1.0% rabbit serum albumin
   0.132 M glucose-6-phosphate
   0.0518 M $\beta$-NAD$^\oplus$
   (pH 5.1)

3. Enzyme Reagent is a dilution of analyte-G6PDH conjugate in:
   0.055 M Tris-HCl
   0.05% NaN$_3$
   0.005% Na$^\oplus$ thimerosal
   0.90% NaCl
   1.0% rabbit serum albumin
   (pH 8.0)

4. Blank Reagent is the diluent from which Enzyme Reagent is prepared. Enzyme Reagent and Blank Reagent are in a sense matched reagents since they are derived from the same lot of diluent:
   0.055 M Tris-HCl
   0.05% NaN$_3$
   0.005% Na$^\oplus$ thimerosal
   0.90% NaCl
   1.0% rabbit serum albumin
   (pH 8.0)

5. Quench Reagent is a 1:5 dilution of a blend of three anti-G6PDH IgG fractions. Bleeds of anti-G6PDH were diluted to give a reagent which additionally contains:
   0.055 M Tris-HCl
   0.05% NaN$_3$
   0.005% Na$^\oplus$ thimerosal
   0.90% NaCl
   1.0% Dextran T-70
   (pH 8.0)

6. 5x Assay Buffer Concentrate when diluted five-fold with distilled water results in Assay Buffer which consists of:
   0.30 M Tris-HCl
   0.05% EDTA.4 Na$^\oplus$.2H$_2$O
   0.05% NaN$_3$
   0.005% Na$^\oplus$ thimerosal
   0.5% NaCl
   0.50% Triton X-100
   0.90 mg/ml Na$^\oplus$ oxamate
   (pH 8.50)

The protocol is as follows. A 40 $\mu$l specimen suspected of containing digoxin is combined with 200 $\mu$l of activated pretreatment solution and the mixture incubated for 20 min. This is followed by the addition of 40 $\mu$l of antibody reagent and 200 $\mu$l of assay buffer, which is followed by a 10 min. incubation. Next, 40 $\mu$l of enzyme reagent or 40 $\mu$l of blank reagent plus 200 $\mu$l of assay buffer is added followed by a 10 to 20 min. incubation depending upon the time desired for the assay. When the assay reaction is to be stopped, 40 $\mu$l of quench reagent plus 200 $\mu$l of assay buffer are added to provide a total volume of 960 $\mu$l and the reaction may be read at any time. The reading is at 340 nm, at room temperature.

The first study concerned the analyte digoxin. The reagents indicated above were employed, wherein the pretreatment reagent had $2.52 \times 10^4$ U/ml of pepsin activity; the antibody reagent was a 1:25000 dilution of an anti-digoxin IgG fraction and the enzyme reagent was 1:4900 dilution of a digoxigen-G6PDH conjugate which was 36.7% deactivated and 75.3% inhibitable, while the quench reagent was a 1:5 dilution of a blend of four different anti-G6PDH IgG fractions.

The calibrators which were employed for relating the change in optical density to concentration of digoxin were prepared using raw human serum which had been dextran sulfate-treated and then dialyzed against phosphate-buffered saline. The calibrator concentrations were 0, 0.50, 1.0, 2.0, 4.0 and 6.0 ng/ml digoxin.

Reproducibility was determined by quantitating 18 to 22 replicates of a given calibrator level per batch. Drift was determined from a regression line and is given as ng/ml digoxin change and as arbitrary units referred to as EMIT ® units change over a full batch (30 specimens). The results of the study are shown in the following table.

TABLE 1

| [DIGOXIN] ng/ml SPIKED | N | $\overline{A} - A_{BLANK}$ | $\sigma$ | % CV |
|---|---|---|---|---|
| 0 | 18 | 1038 | 2.51 | 0.24 |
| 0.50 | 18 | 1114 | 2.53 | 0.23 |
| 1.0 | 18 | 1067 | 3.51 | 0.33 |
| 2.0 | 18 | 1157 | 2.62 | 0.23 |
| 4.0 | 18 | 1171 | 1.91 | 0.16 |
| 6.0 | 22 | 1327 | 3.59 | 0.27 |

| [DIGOXIN] ng/ml | $\sigma$ | % CV | DRIFT ng/ml | DRIFT EMIT UNITS |
|---|---|---|---|---|
| — | — | — | — | 3.7 |
| 0.48 | 0.04 | 7.38 | −0.03 | −1.5 |
| 1.05 | 0.07 | 6.51 | −0.15 | −7.6 |
| 2.07 | 0.07 | 3.39 | −0.03 | −1.0 |
| 3.91 | 0.09 | 2.28 | −0.23 | −5.1 |
| 5.80 | 0.19 | 3.36 | 0.10 | 1.7 |

Despite the extremely low concentration of digoxin which is present, the reproducibility is as good as commercially available assays.

In the next study, 260 patient samples were taken and the subject assay compared to a commercially available EIA (enzyme immunoassay) employing an ABA instrument and a commercially available RIA (radioimmunoassay) Gammacoat ® available from Clinical Assays. In each case certain of the patient samples were not employed either because of being severally lipemic, hemolyzed or quantitating above 4 ng/ml. The following table indicates the slope, intercept, correlation, S.E.E.

and the number of samples comparing the subject assay against the other two assays.

TABLE 2

|  | Subject Assay vs | |
|---|---|---|
|  | EIA | RIA |
| Slope | 1.056 | 1.039 |
| Intercept | 0.008 | 0.090 |
| Correlation | 0.926 | 0.898 |
| S.E.E. | 0.23 | 0.24 |
| N | 240 | 241 |

It is evident from the above results, that the subject assay tracks closely with commercially available assays for the same analyte, digoxin. Thus, the subject assays provide the convenience of avoiding a rigid schedule of measurements.

In the next study, the analyte was cortisol. The antibody reagent was a 1:6000 dilution of anti-cortisol IgG fraction, the enzyme reagent was a 1:1000 dilution of a cortisol-G6PDH conjugate (see U.S. Pat. No. 3,817,837 for method of preparation) (50–60% deactivated and 70% inhibitable) and the calibrators were prepared using charcoal treated, Freon ® treated human serum, with the calibrator concentrations being 0, 2.0, 5.0, 10.0, 20.0, and 40 μg/dl of cortisol. In addition, the pretreatment time was 5 mins. and there was no incubation time between the addition of the antibody reagent and the addition of the enzyme reagent.

For the five cortisol calibrators having cortisol present, the following table indicates the results.

TABLE 3

| [Cortisol] ug/dl | 40 | 20 | 10 | 5 | 2 |
|---|---|---|---|---|---|
| N | 20 | 21 | 20 | 20 | 22 |
| $\bar{A} - A_{BLANK}$ | | | | | |
| Mean | 1150.15 | 1105.31 | 1081.58 | 1039.25 | 989.05 |
| S.D. | 4.06 | 3.25 | 1.76 | 2.35 | 2.71 |
| Slope | −0.1333 | −0.0633 | −0.094 | +0.0598 | −0.0667 |
| CV % | 0.35 | 0.29 | 0.16 | 0.23 | 0.27 |
| Drift in EMIT Units | −4.0 | −1.9 | −2.8 | 1.8 | −2.0 |

The subject assay for cortisol was then compared with a commercially available RIA for cortisol and the assay carried out at 24° C. The following table indicates the results.

TABLE 4

| Subject Assay vs RIA | |
|---|---|
| Slope | 1.020 |
| Intercept | −0.171 |
| Correlation | 0.979 |
| S.E.E. | 1.60 |
| N | 23 |

It is evident from the above results, that the subject assay provides for an accurate and quantitative determination of cortisol.

The subject assay provides for a number of advantages. If one wishes a semi-quantitative determination, one can run a control and the subject sample simultaneously and terminate the two assays simultaneously. Therefore, no critical timing need be involved, since the two samples will be treated comparably. Temperature control can also be avoided by assaying for calibrators and samples simultaneously. Readings can be conveniently organized at the pleasure of the clinician. The employment of an antienzyme is extremely convenient, since it may be easily added, rapidly takes effect, and does not interfere with the observed signal level.

Although the foregoing invention has been described in some detail by way of illustration and example for purposes of clarity of understanding, it will be obvious that certain changes and modifications may be practiced within the scope of the appended claims.

What is claimed is:

1. In an enzyme immunoassay for haptens employing enzyme-hapten conjugates, where said enzyme is NAD or NADP dependent with the amount of antihapten binding to the hapten being related to the amount of hapten in a sample added to an assay medium, and determining the amount of hapten by analyzing for the change in concentration of an enzyme cofactor which is NAD, NADP or the reduced form thereof,
   wherein the assay is performed by combining said sample, said enzyme-hapten conjugate, a hapten receptor, and an enzyme substrate resulting in said enzyme cofactor, in an aqueous buffered medium; and allowing sufficient time for transformation of said enzyme substrate;
   the improvement which comprises:
   quenching said transformation by the addition of antienzyme to the assay medium at the end of said sufficient time.

2. In a homogeneous enzyme immunoassay for haptens employing enzyme-hapten conjugates, where antihapten binding to the hapten results in a substantial change in the activity of the enzyme, with the amount of antihapten binding to the hapten being related to the amount of hapten in a sample added to an assay medium, and determining the amount of hapten by analyzing for the change in concentration of an enzyme cofactor which is NAD, NADP or the reduced forms thereof,
   wherein the assay is performed by combining the sample, said enzyme-hapten conjugate, hapten receptor, and an enzyme substrate resulting in said enzyme cofactor, in an aqueous buffered medium; and allowing sufficient time for transformation of said enzyme substrate;
   the improvement which comprises:
   quenching said transformation by the addition of antienzyme to the assay medium at the end of said sufficient time.

3. A method according to claim 2, wherein said enzyme is a NAD or NADP dependent dehydrogenase.

4. A method according to claim 3, wherein said dehydrogenase is glucose-6-phosphate dehydrogenase.

5. A method according to any of claims 1 to 4, wherein said chemically labile compound which is determined is H or NADPH.

6. A method according to any of claims 1 to 5, wherein said hapten is a steroid.

7. A method according to claim 6, wherein said steroid is digoxin.

8. A method according to claim 6, wherein said steroid is cortisol.

9. In a homogeneous enzyme immunoassay method comprising: combining a sample suspected of containing a steroid, glucose-6-phosphate-hapten conjugate, antisteroid and substrates for said conjugate including NAD or NADP; and
   allowing the enzyme to convert NAD or NADP for a predetermined time; and
   measuring the amount of converted NAD or NADP; the improvement comprising:
   quenching said conjugate with anti(glucose-6-phosphate dehydrogenase) so that the amount of converted NAD or NADP remains substantially constant over an extended period of time.

* * * * *